United States Patent
Ropital et al.

(10) Patent No.: US 7,246,516 B2
(45) Date of Patent: Jul. 24, 2007

(54) DEVICE FOR COUPLING THERMOGRAVIMETRIC ANALYSES AND ACOUSTIC EMISSION MEASUREMENTS

(75) Inventors: Francois Ropital, Rueil Malmaison (FR); Philippe Dascotte, Saint Gratien (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 11/207,943

(22) Filed: Aug. 22, 2005

(65) Prior Publication Data

US 2006/0037386 A1     Feb. 23, 2006

(30) Foreign Application Priority Data

Aug. 20, 2004 (FR) ................... 04 09039

(51) Int. Cl.
   *G01N 17/00*     (2006.01)
(52) U.S. Cl. ............... 73/86; 73/865.6; 73/587; 436/6; 422/53
(58) Field of Classification Search ............ 73/86, 73/587, 865.6; 436/6; 422/53
   See application file for complete search history.

(56) References Cited

U.S. PATENT DOCUMENTS

| | | | | |
|---|---|---|---|---|
| 4,510,812 A | * | 4/1985 | Feng | ............... 73/644 |
| 5,000,045 A | * | 3/1991 | Secoy | ............... 73/587 |
| 5,526,689 A | * | 6/1996 | Coulter et al. | ............... 73/592 |
| 6,057,516 A | * | 5/2000 | Nakamura et al. | ............... 177/212 |
| 2003/0019328 A1 | * | 1/2003 | Dunmead et al. | ............... 75/392 |

FOREIGN PATENT DOCUMENTS

DE     44 44 944 A1     6/1996

OTHER PUBLICATIONS

Baldev Raj et al., "Acoustic Emission Studies Towards Better Understanding of High Temperature Oxidation In Cr-Mo Steels", International Journal Of Pressure Vessels and Piping UK, vol. 45, No. 3, 1991, pp. 301-326.

* cited by examiner

*Primary Examiner*—Hezron Williams
*Assistant Examiner*—Samir M. Shah
(74) *Attorney, Agent, or Firm*—Antonelli, Terry, Stout & Kraus, LLP.

(57) ABSTRACT

The present invention relates to a device comprising a thermobalance equipped with a detector (5) for measuring acoustic signals emitted by a sample (6) hanging from the balance beam and a preamplifier (2) incorporated in the vicinity of the head of the balance. The invention allows gas phase kinetic study of the degradation of materials and of depositions on these materials under temperature (100 to 1400° C.). In particular, corrosion phenomena such as: oxidation, sulfurization, carbonizing, metal dusting, nitriding, hydridation, chlorination, molten salt attack, and combinations of these degradations. Besides, deposits on the materials can be due to coking phenomena (carbon deposits), deposition of molten salts, volatile compounds condensation. The invention allows evaluation of the efficiency of inhibitors against corrosion and deposition processes.

2 Claims, 4 Drawing Sheets

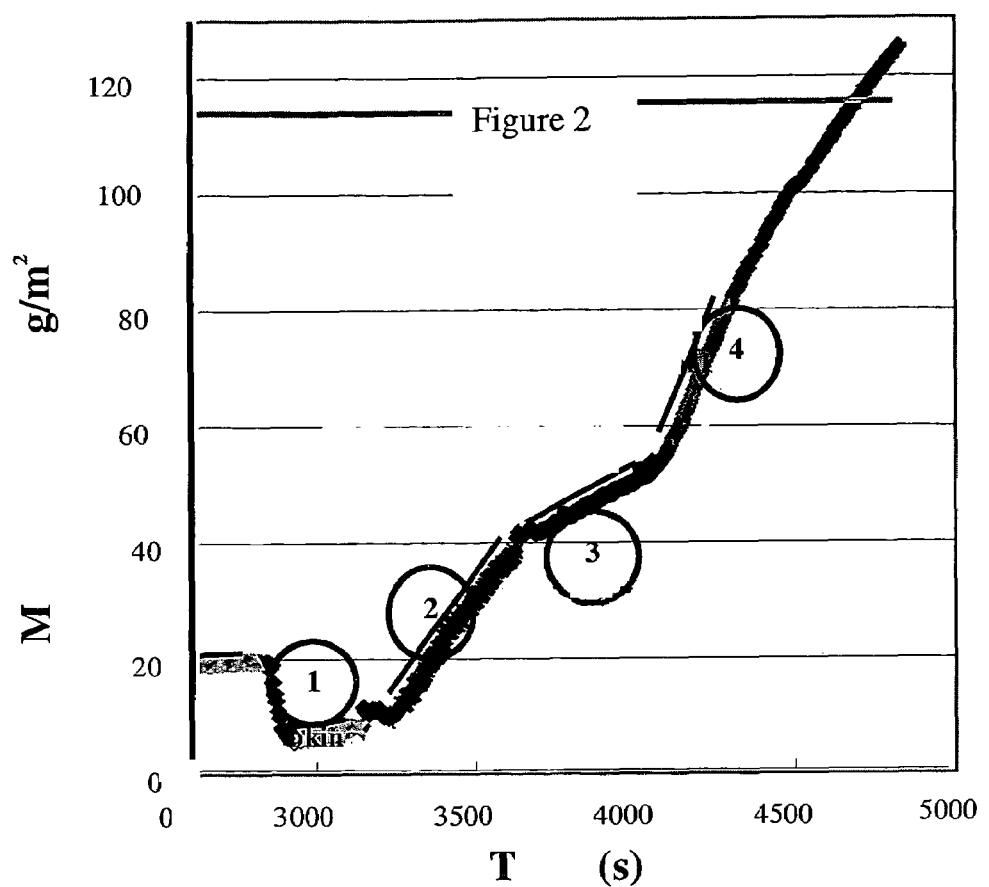

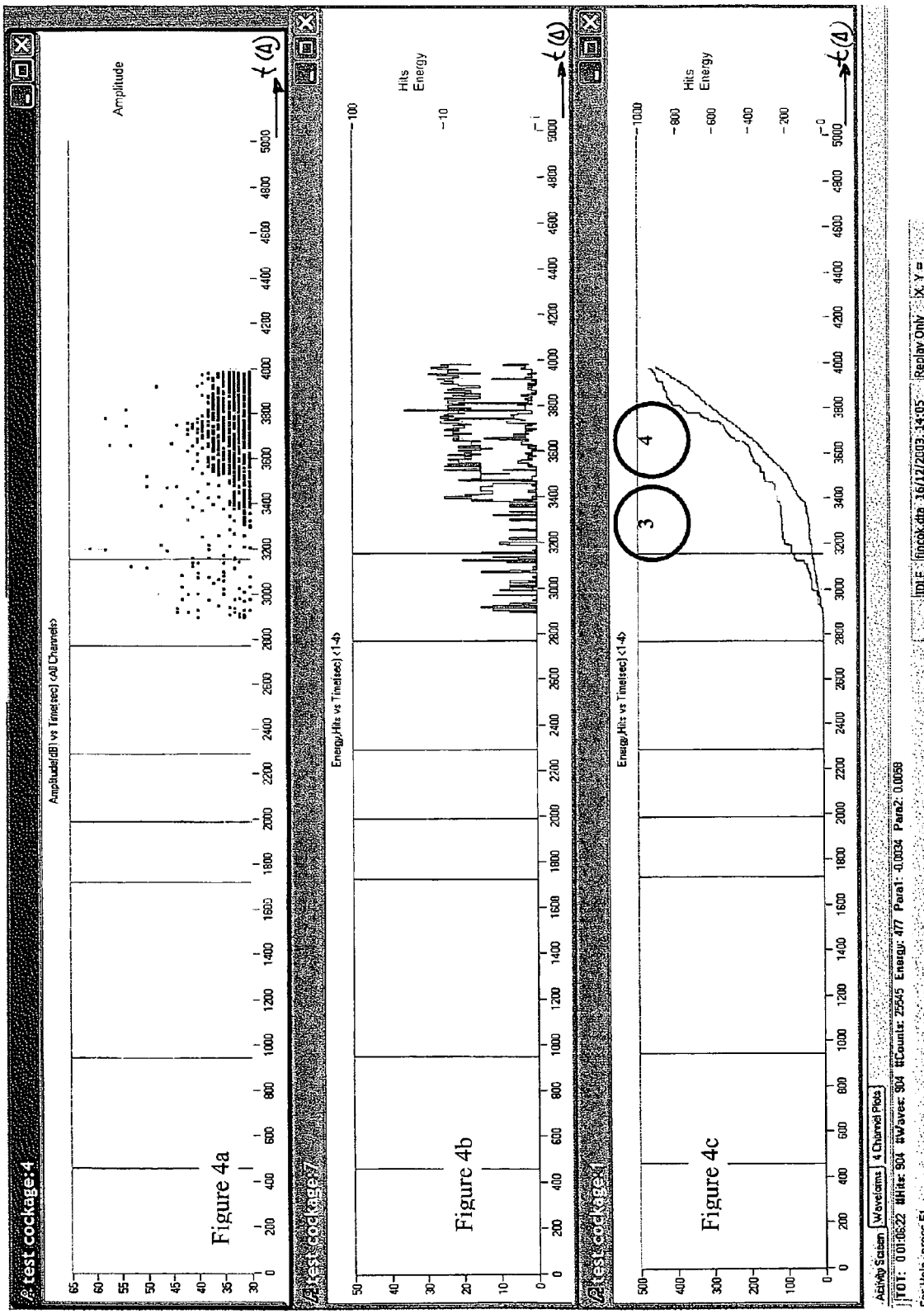

DEVICE FOR COUPLING THERMOGRAVIMETRIC ANALYSES AND ACOUSTIC EMISSION MEASUREMENTS

BACKGROUND OF THE INVENTION

1. Field of the Invention

The present invention relates to the field of the study of materials subjected to very high temperatures, notably in a degrading atmosphere.

2. Description of the Prior Art

Industrial equipments working under high temperatures (above 200° C.) are frequently subjected to environments likely to cause corrosions and degradations of the materials they consist of, and depositions on the surface thereof. In order to ensure reliability of these equipments, it is necessary to control these phenomena such as: oxidation, sulfurization, carbonizing, metal dusting, nitriding, hydriation, chlorination, molten salt attack, and combinations of these degradations. The deposits likely to form on the equipment walls are notably: carbon-containing products (coke), molten salts, volatile compound condensations.

In order to select suitable materials and to monitor their behavior, thermogravimetric analyses (TGA) are commonly used. These analyses are carried out in specific devices referred to as thermobalances, where the conditions of the industrial environment are reproduced to allow continuous determination of the evolution of the mass of a material sample as a function of time.

Acoustic emissions were used so far to control the generalized and localized corrosion of metallic materials immersed in electrolytes. Some studies ("F. Ferrer, J. Goudiakas, E. Andres and C. Brun, Nace Corrosion 2001 Conference, Paper 01386"; and "M. Schulte, A. Rahmel and M. Schutze, *Oxidation of metals*, 49 (1998) 33") tried to use large acoustic emission detectors to evaluate the behaviour of tube sections in pilot plants.

The present invention relates to a device comprising a specific thermobalance allowing to measure, together with the mass variation of the sample, acoustic signals emitted by the sample. The information, compared, recorded and subjected to real-time processing, allows to optimize the material behavior analyses and to simplify industrial monitoring thereof, notably by means of an analysis of the phenomena kinetics.

SUMMARY OF THE INVENTION

The present invention thus relates to a device for analyzing the corrosion and/or deposits on a material sample, comprising means for measuring the mass variation of the material. The device comprises a thermobalance equipped with a rod for suspending the sample, the rod comprising a detector measuring the acoustic signals emitted by the sample, the detector being connected to amplification means incorporated in the head of the balance.

The detector can be arranged outside the thermobalance oven and have a determined geometry so as not to unbalance the gravimetric measurement.

The resonant frequency of the detector can be about 300 kHz.

The amplification means can include a preamplifier designed for filtering a passband between 100 and 300 kHz, and arranged as close as possible to the detector to amplify its signals.

The invention also relates to the application of the device to the gas phase kinetic study of the temperature degradation of materials (100-1400° C.), such as the following corrosion phenomena: oxidation, sulfurization, carbonizing, metal dusting, nitriding, hydriation, chlorination, molten salt attack, and combinations of these degradations.

The device can also be applied to the gas phase kinetic study of depositions on materials under temperature (100-1400° C.), such as coking (carbon-containing deposits), deposition of molten salts, volatile compounds condensation.

The device can also be applied to the study of the efficiency of inhibitors against corrosion and deposition processes.

BRIEF DESCRIPTION OF THE DRAWINGS

Other features and advantages of the invention will be clear from reading the description hereafter of an embodiment given by way of non limitative example, with reference to the accompanying figures wherein:

FIGS. 2, 3a and 3b and 4a, 4b and 4c show measurement examples and their application.

DETAILED DESCRIPTION OF THE INVENTION

Many physical phenomena and material damage mechanisms are the cause of the emission of transient elastic acoustic waves, for example:

particle impacts,
cavitation,
friction,
chemical surface attack (corrosion),
diffusion of foreign elements in the material (hydrogen, carbon, oxygen, nitrogen),
initiation and propagation of cracks (case of stress corrosion).

Measurement of the acoustic emission generated by a material under degradation can be described in two stages: detection of the acoustic wave and analysis of the acoustic emission data in real and deferred time a. Acoustic Wave Detection In general, piezoelectric detectors which convert the surface displacement caused by the acoustic wave (coming from the acoustic emission source) to an electric signal are used. These detectors are coupled with the surface of the material. The acoustic emission signal is then conditioned by a preamplifier whose functions are as follows:

electric impedance matching,
amplification,
filtering.

The acoustic emission signal is then transmitted to the measuring system (or acquisition chain) by a coaxial cable.

Then, the next operation is the detection of exceeding of a threshold. The signals are compared with an adjustable detection threshold. When the device detects that this detection threshold has been exceeded, the parameters characteristic of the acoustic emission signals (bursts) are measured.

The background noise and the level of the continuous acoustic emission are generally measured by a physical quantity obtained by averaging the signal (rms value, ASL values, . . . ).

The base parameters measured on each burst are as follows:

arrival time (threshold exceeding detection time),
maximum amplitude (expressed in $dB_{AE}$),
number of shots, duration,
rise time,
energy.

These parameters are collected on each measuring channel independently and for each detected burst. They are then transmitted to the recording and computing system (generally a microcomputer).

b. Real and Deferred Time Analysis of the Acoustic Emission Data

Once the acoustic emission data are stored, suitable processings are applied in order to evaluate the measurement results. These processings relate to the burst parameters (historical and statistical analyses), and they also (generally) allow grouping of the bursts detected by the various measuring channels so as to calculate the position of the acoustic emission sources.

Reference to the NF EN 1330-9 standard should be made for the terms used in the acoustic emission technique.

The present invention relates to the setting of a miniaturized piezoelectric detector and of a miniaturized preamplifier allowing use in small volumes such as those encountered in thermobalance oven tubes (diameter below 20 mm).

Figure 1:
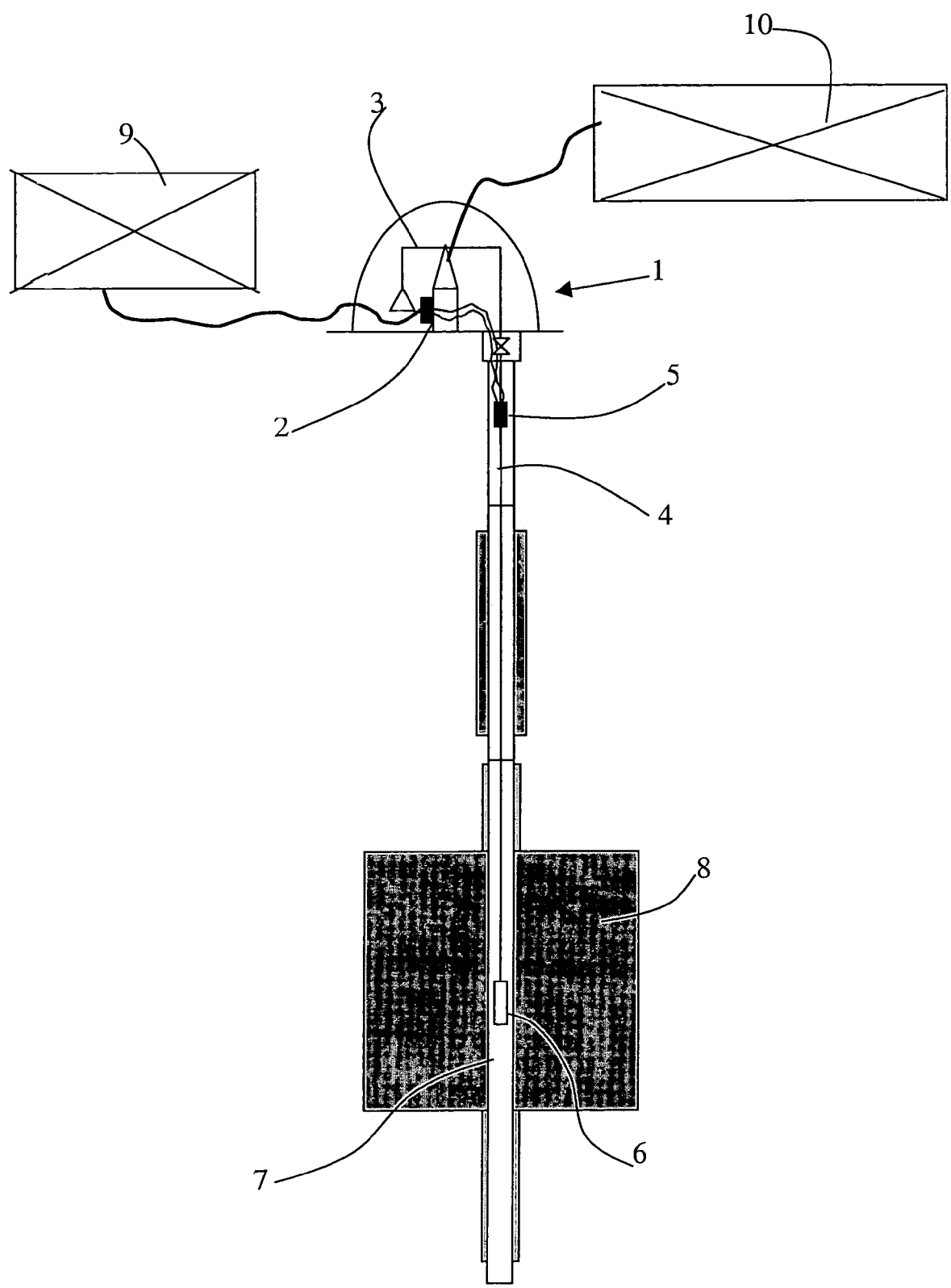
FIG. 1 shows a diagram of the device.

FIG. 1 diagrammatically describes the device according to the invention. This device includes:
a thermobalance head 1 of sensitivity 0.001 mg containing a preamplifier 2 for emission signals EA,
a beam 3 from which a suspension rod for the sample being studied hangs,
a suspension rod 4 to which a metallic sample 6 is fastened at one end thereof, and onto which an acoustic emission EA detector 5 is positioned close to the other end of the rod,
a tubular reactor 7 placed in oven 8 (20-1000° C.) of the thermobalance,
an acoustic signal acquisition and processing chain 9,
an acquisition chain 10 intended for acquisition of the thermobalance mass variation measurements.

Detector 5 is a specific piezoelectric 300-kHz resonant frequency acoustic emission detector. It is positioned on the upper end of suspension rod 4 in a zone where the temperature does not exceed 150° C. This detector was designed so as not to disturb the balance equilibrium and the measurement of the sample mass variation. The suspension rod and the detector were adapted in such a way that the acoustic emission signal is propagated along the suspension rod and this signal can be detected with an allowable noise/signal.

A miniaturized preamplifier 2 was designed so as to filter (100-300 kHz passband) and to amplify the acoustic signal (40 dB). It is arranged as close as possible to acoustic emission detector 5 in the thermobalance head and it is connected to the detector by flexible insulated wires.

Tests 10 mm×5 mm×1 mm samples made of pure iron and steel were machined. Prior to being fed into the oven, they are polished mechanically with abrasive paper until a 1200 grain size is obtained. They are then cleaned with ethanol. One of them is fastened to an end of the suspension rod, which is itself fastened to the thermobalance head. Air heating is established to obtain a temperature of 650° C. in the tubular reactor of the thermobalance. When this temperature is reached, a hydrogen-isobutane (30% $H_2$, 30% $iC_4H_{10}$, 40% Ar) carbonizing atmosphere representative of industrial refining conditions is introduced. The composition of the gaseous mixture and its flow rate (50 ml/min) are controlled by mass flowmeters. The carbon activity is then 6700, causing formation of coke deposits at the surface of the metallic sample. In order to limit this coking phenomenon, hydrogen sulfide is added to the feed in small amounts (3 ppm).

Experimental Results

From the TGA measurements of the sample mass variation, a coking rate is calculated by measuring the slope of the curve giving mass variation M ($g/m^2$) as a function of time T (s) as shown in the diagram of FIG. 2.

Coking sequences (No. 1 to 4) with or without hydrogen sulfide addition (3 ppm) were carried out. For these various periods, the coking rates (Table 1) were measured and the acoustic emission signals recorded.

TABLE 1

Coking rate of iron at 650° C. for the various sequences

| Period | Coking rate ($g/m^2h$) |
| --- | --- |
| No. 1: feed with $H_2S$ | 25 |
| No. 2: feed without $H_2S$ | 270 |
| No. 3: feed with $H_2S$ | 106 |
| No. 4: feed without $H_2S$ | 480 |

Period No.1

Figures 3A, 3B:
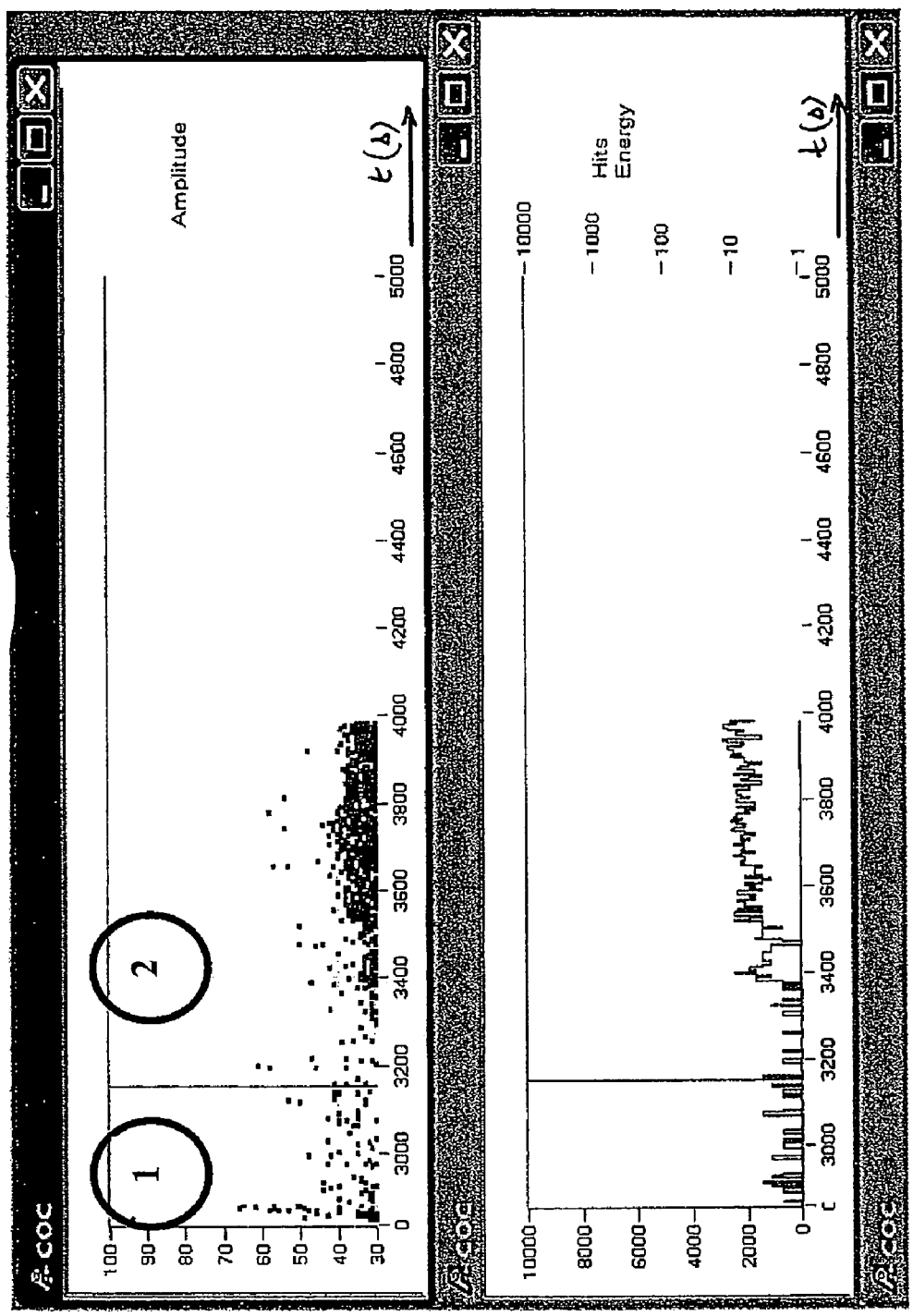

The coking rate is low and coking is well inhibited by the addition of hydrogen sulfide. The acoustic emission signals are very weak, as regards the number of bursts as well as their amplitude (FIG. 3a and FIG. 3b).

Period No.2

Injection of coking inhibitor (hydrogen sulfide) is stopped. The coking rate is 10 times as high as that of period 1. The density of the acoustic emission bursts is greatly increased (FIG. 3a), which is translated into high activity and energy rates (FIG. 3b).

Period No.3

The coking rate is reduced by half and coking is well inhibited by the addition of hydrogen sulfide. The acoustic emission signals, as regards the number of bursts as well as their amplitude, are weak again (FIGS. 4a, 4b, 4c).

Period No.4

Injection of coking inhibitor (hydrogen sulfide) is stopped. The coking rate is 4 times as high as that of period 3. The density of the acoustic emission bursts is greatly increased (FIG. 4a), which is translated into high activity and energy rates (FIGS. 4b, 4c).

A good match is thus observed between the TGA measurements and the acoustic emissions (number of bursts and energy level). Thus, in particular under carbonizing conditions, the acoustic emissions should allow coking control.

The invention claimed is:

1. A method of study of temperature depositions in a range between 100 and 1400° C. on materials using a device including means for measuring a mass variation of a material sample, including a thermobalance equipped with a rod for suspending a material sample, the rod comprising a detector for measuring acoustic signals emitted by the material sample, the detector being connected to an amplification means incorporated in a head of the balance comprising:

selecting the material sample with a deposition selected from the group consisting essentially of coking, deposition of molten salts or volatile compound deposition; and measuring the acoustic signals emitted from the deposition to study the temperature deposition on the selected material sample.

2. A method of study using a device including means for measuring a mass variation of a material sample, including a thermobalance equipped with a rod for suspending a material sample, the rod comprising a detector for measuring acoustic signals emitted by the material sample, the detector being connected to an amplification means incorporated in a head of the balance comprising:

selecting a corrosion or deposition process inhibitor; and measuring the acoustic signals emitted from the material sample contacted by the corrosion or deposition process inhibitor to study the corrosion or deposition process inhibitor.

* * * * *